US010209500B2

United States Patent
Huang et al.

(10) Patent No.: US 10,209,500 B2
(45) Date of Patent: *Feb. 19, 2019

(54) THREE-DIMENSIONAL OPTICAL COHERENCE TOMOGRAPHY APPARATUS AND ITS APPLICATION

(71) Applicant: NATIONAL TAIWAN UNIVERSITY, Taipei (TW)

(72) Inventors: Sheng-Lung Huang, Taipei (TW); Tuan-Shu Ho, Taipei (TW); Chien-Chung Tsai, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,449

(22) Filed: Jul. 6, 2017

(65) Prior Publication Data

US 2017/0371137 A1 Dec. 28, 2017

Related U.S. Application Data

(63) Continuation of application No. 14/816,172, filed on Aug. 3, 2015, now Pat. No. 9,726,872.

(51) Int. Cl.
*G02B 21/00* (2006.01)
*A61B 5/00* (2006.01)
*G02B 21/02* (2006.01)

(52) U.S. Cl.
CPC ........ *G02B 21/0056* (2013.01); *A61B 5/0066* (2013.01); *G02B 21/0092* (2013.01); *G02B 21/02* (2013.01)

(58) Field of Classification Search
CPC ............ G02B 21/0056; G02B 21/0092; G02B 21/02; A61B 5/0066; A61B 5/0068; A61B 5/0071; A61B 5/0073; A61B 5/0075
USPC ......................................... 359/370, 371, 656
See application file for complete search history.

(56) References Cited

U.S. PATENT DOCUMENTS

| 9,213,174 B2* | 12/2015 | Kaneki | G02B 21/0092 |
| 2002/0018291 A1* | 2/2002 | Fukuyama | G02B 21/002 359/368 |
| 2007/0238955 A1* | 10/2007 | Tearney | A61B 1/00096 600/407 |
| 2011/0310395 A1* | 12/2011 | Tsai | G01B 9/02091 356/479 |
| 2013/0301006 A1* | 11/2013 | Kim | A61B 3/102 351/206 |

(Continued)

FOREIGN PATENT DOCUMENTS

EP 2728549 * 5/2014 ............... G01B 9/02

OTHER PUBLICATIONS

Record for optical long-wave-pass filters from Spectrogon at https://www.spectrogon.com/product-services/optical-filters/spectrogon-us/longwave-pass-filters/ published on Jun. 15, 2013.*

(Continued)

*Primary Examiner* — Frank G Font
(74) *Attorney, Agent, or Firm* — Chang-Hsing Liang

(57) ABSTRACT

Provided herein are devices and systems that apply full-field optical coherence tomography (OCT) technology to three-dimensional skin tissue imaging. A special designed Mirau type objective and an optical microscope module allowing both OCT mode and orthogonal polarization spectral imaging (OPSI) mode are disclosed.

19 Claims, 7 Drawing Sheets

(56) References Cited

U.S. PATENT DOCUMENTS

2014/0049815 A1* 2/2014 Kusaka ............... G02B 21/14
359/371
2014/0118820 A1* 5/2014 Kaneki ............. G02B 21/0092
359/386

OTHER PUBLICATIONS

Tsai et al., "Full-depth epidermis tomography using a Mirau-based full-field optical coherence tomography", Biomedical Optics Express, vol. 5, No. 9, Aug. 8, 2014 (Aug. 8, 2014), pp. 3001-3010.*
Cerny et al., "Orthogonal polarization spectral imaging", Physiological research/ Academia Scientiarum Bohemoslovaca, Jan. 1, 2007 (Jan. 1, 2007), pp. 141-147.*
Lu, et al., "Full-field optical coherence tomography using immersion Mirau interference microscope", Applied Optics, Optical Society of America, Washington, DC; US, vol. 52, No. 18, Jun. 20, 2013 (Jun. 20, 2013), pp. 4400-4403.*
Chen, et al., "Polarization memory effect in optical coherence tomography and dental imaging application", Journal of Biomedical Optics, vol. 16, No. 8, Aug. 30, 2011 (Aug. 30, 2011).*

* cited by examiner

THREE-DIMENSIONAL OPTICAL COHERENCE TOMOGRAPHY APPARATUS AND ITS APPLICATION

BACKGROUND OF THE INVENTION

Optical Coherence Tomography (OCT) is a technique for performing high resolution cross-sectional imaging that can provide images of tissue structure (e.g., skin tissues) on the micron scale. OCT method measures light-scattering specimens on their inside along the OCT beam.

Mohs micrographic surgery is excised from a patient under microscopic control for the complete excision of basal cell carcinoma (BCC), squamous cell carcinoma (SCC), and less commonly other types of skin cancer. The excised tissue specimen (i.e., a biopsy) is horizontally sliced to provide tissue sections which are then histologically prepared on slides. The slides are reviewed under a microscope to determine whether the tumor is fully contained in the excised tissue determined by the absence of the tumor in the edges or margins of the excised tissue. If the tumor is not fully contained in the excised tissue, additional tissue from the patient is excised and the procedure repeated until all tissue sections taken indicate the tumor has been removed from the patient. Biopsy and histological processing is the gold standard for tissue diagnosis. Thus Mohs surgery in general is very time consuming because it requires many biopsies. Application of OCT to create images of Mohs micrographic surgery specimens in an efficient way is thus very helpful.

SUMMARY OF THE INVENTION

The present invention provides devices or systems comprising a light source module configured to provide a source light to an optical microscope module, which handles the source light and processes light signal; a Mirau type objective module, which handles light from the optical microscope module and process light signal generated from a tissue translation module holding the tissue sample; and a data processing unit for analyzing light signals from the tissue sample, wherein said Mirau type objective module comprises an interference objective immersed in a media with optical characteristics close to the tissue sample, and wherein said optical microscope module comprises an optical switch configured to toggle between optical coherence tomography (OCT) mode and orthogonal polarization spectral imaging (OPSI) mode.

In another aspect provides a method for imaging a tissue sample comprising imaging test light in depth emerging from a sample, and imaging a contrast image of absorption, dispersion, and/or scattering from a substructure of the sample to provide a dynamic state of the sample, by a device or a system described herein.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are used, and the accompanying drawings of which.

DETAILED DESCRIPTION OF THE INVENTION

Figure 1:
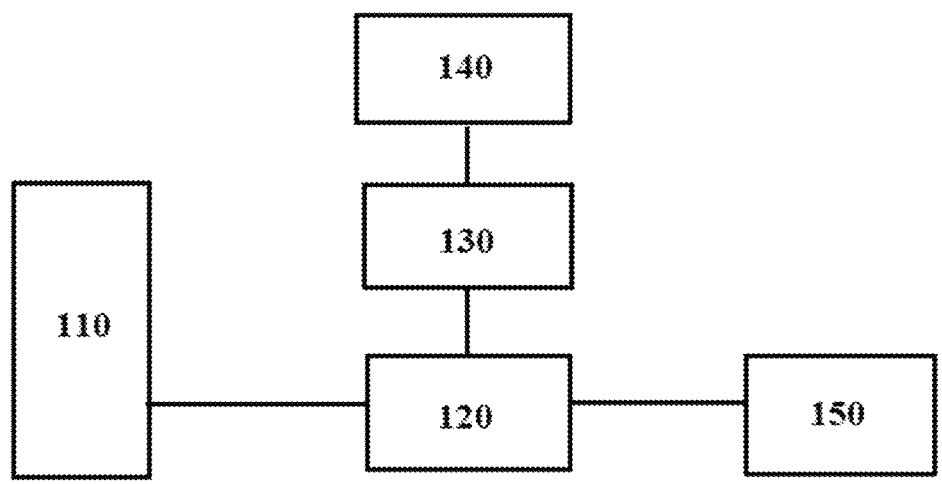
FIG. 1 illustrates a block diagram representing the invention device/system comprising a light source module, an optical microscope module, a Mirau type objective module, a tissue translation module, and a data processing unit.

In recent years, optical coherence tomography (OCT) has been widely applied on three-dimensional (3-D) image reconstruction of skin tissue. It is known that in epidermis, to non-invasively probe the layer parameters (LPs), such as average total thickness (a-TT), average number of layers (a-NOLs), and average cellular layer thickness (a-CLT), for stratum corneum (SC) becomes important for evaluating the skin moisturization of epidermis. However, to apply OCT technology to skin tissue imaging, axial resolution better than 1.2 µm in tissue is the doorsill to measure LPs of the SC. Besides, the morphology of single 3-D epidermal cell is also important for early detection of normal and abnormal cells of pre-cancer diagnosis. These all require sub-micron spatial resolution in tissue. Full-field OCT (FF-OCT) utilizing two-dimensional CCD/CMOS camera has the opportunity to observe the layer structure of SC, especially for en face monitoring. Typically, the detection sensitivity of FF-OCT using CCD/CMOS camera is about 80 dB, related to the camera area size and en face frame rate.

Keratinocyte and melanocyte are the two major cell types in epidermis, with a normal size from 10 to 50 µm. The epidermis can be divided into several layers, which are stratum basale at the bottom, stratum spinosum, stratum granulosum, stratum lucidum, and SC on the top, through keratinization process within about one month. In epidermis, melanocytes are interspersed at stratum basale with stretching dendrites. For skin care aspect, the proliferation and differentiation of keratinocyte affect the capability of epidermal moisture lock and dry skin disease.

Provided herein are devices and systems that apply OCT technology (e.g., a FF-OCT) to skin tissue imaging. In particular, the present invention provides 3-D imaging of a skin tissue in vitro and in vivo.

In some embodiments, there are provided a device comprising a light source module configured to provide a source light to an optical microscope module, which handles the source light and processes light signal; a Mirau type objective module, which handles light from the optical microscope module and process light signal generated from a tissue translation module holding a tissue sample; and a data processing unit for analyzing light signals from the tissue sample, wherein said Mirau type objective module comprises an interference objective immersed in a media, and wherein said optical microscope module comprises an optical switch configured to toggle between optical coherence tomography (OCT) mode and orthogonal polarization spectral imaging (OPSI) mode.

In some embodiments, the light source module comprises a spontaneous emission light source, an amplified spontaneous emission light source, a superluminescent diode, a light emitting diode (LED), a broadband supercontinuum light source, a mode-locked laser, a tunable laser, a Fourier-domain mode-locked light source, an optical parametric oscillator (OPO), a halogen lamp, or a doped crystal fiber such as a $Ce^{3+}$:YAG crystal fiber, a $Ti^{3+}$:$Al_2O_3$ crystal fiber, or a $Cr^{4+}$:YAG crystal fiber. In certain embodiments, the light source module comprises a $Ce^{3+}$:YAG crystal fiber, $Ti^{3+}$:$Al_2O_3$ crystal fiber, or a $Cr^{4+}$:YAG crystal fiber. In certain embodiments, the light source module comprises a $Ce^{3+}$:YAG crystal fiber.

In some embodiments, the Mirau type objective module comprises an interference objective lens immersed in a media, a first glass plate, a second glass plate in a sealed container filled with one or more media. In certain embodiments, the interference objective lens immersed in a media having optical characteristics similar to the tissue sample to be analyzed. In certain embodiments, the optical characteristics is refractive index. In certain embodiments, the media has a refractive index in a range of about 1.2 to about 1.8. In certain embodiments, the media has a refractive index in a range of about 1.3 to about 1.5. In some embodiments, the media comprises water, silicone oil, ethanol, glycerol, pyrex, a transparent glass or plastic with a refractive index in a range of about 1.3 to about 1.5, or combinations thereof. In certain embodiments, said media comprises water, silicone oil, or glycerol. In certain embodiments, the media comprises water. In certain embodiments, the media comprises silicone oil. In some embodiments, the one or more media comprises a first media and a second media. In certain embodiments, said first media comprises water and the second media comprises silicone oil.

In some embodiments, the optical switch is a quarter-wave plate where the fast axis of the quarter-wave plate is set to an angle of 45° allowing a portion of a signal light reflected or scattered from the sample passing through with polarization state unchanged. In certain embodiments, the optical switch is a quarter-wave plate where the fast axis of the quarter-wave plate is set to an angle of 0° or 90° allowing a portion of a signal light reflected or scattered from the sample passing through with polarization state rotated by 90°. In some embodiments, the optical microscope module further comprises an objective lens, an optical long-wave-pass filter, and a polarization beam splitter.

In some embodiments, the tissue translation module comprises a cover glass and a transversely motorized linear stage on a tissue holder means. In some embodiments, the tissue holder means is a slide or a cartridge. In certain embodiments, the cover glass is acted as the tissue holder.

In some embodiments, the data processing unit comprises a one-dimensional detector, or a two-dimensional detector, optionally coupled a computer, or combinations thereof. In certain embodiments, the data processing unit comprises a two-dimensional detector. In certain embodiments, the two-dimensional detector is a charge-coupled device (CCD), a multi-pixel camera, or a complementary metal oxide semiconductor (CMOS) camera, or combination thereof.

In some embodiments provides a system or a device comprising a $Ce^{3+}$:YAG crystal fiber/LED light source module configured to provide a source light to an optical microscope module, which handles the source light and processes light signal; a Mirau type objective module, which handles light from the optical microscope module and process light signal generated from a tissue translation module; and a data processing unit for analyzing light signals from a tissue sample, wherein said Mirau type objective module comprises silicone oil, and wherein said optical microscope module comprises a quarter-wave plate as an optical switch configured to toggle between optical coherence tomography (OCT) mode and orthogonal polarization spectral imaging (OPSI) mode.

Referring to FIG. 1, an exemplary invention system/device 100 comprising a light source module 110, an optical microscope module 120, a Mirau type objective module 130, a tissue translation module 140, and a data processing unit 150. The light module 120 is configured to provide suitable light to the optical microscope module 120, which handles the source light and processed light signals. The optical microscope module 120 is associated with a Mirau type objective module 130 which further processes and inject the light to a tissue sample at the tissue translation module 140. Light coming back from the tissue translation module is directed to the data processing unit 150.

In some embodiments, the light source module comprises a spontaneous emission light source, an amplified spontaneous emission light source, a superluminescent diode, a light emitting diode (LED), a broadband supercontinuum light source, a mode-locked laser, a tunable laser, a Fourier-domain mode-locked light source, an optical parametric oscillator (OPO), a halogen lamp, or a doped crystal fiber such as a $Ce^{3+}$:YAG crystal fiber, a $Ti^{3+}$:$Al_2O_3$ crystal fiber, a $Cr^{4+}$:YAG crystal fiber, or any other suitable light source a skilled in the art would readily recognized to provide suitable light in accordance with the practice of the present invention. In certain embodiments, the light source module comprises a $Ce^{3+}$:YAG crystal fiber, a $Ti^{3+}$:$Al_2O_3$ crystal fiber, or a $Cr^{4+}$:YAG crystal fiber. The light source module, such as those disclosed in U.S. Pat. Nos. 8,416,48, 8,625,948 and U.S. Publication No. 20080047303 (each of which are incorporated herein by reference for such disclosure) are known.

In some embodiments, the data processing unit comprises a one-dimensional detector, a two-dimensional detector, or a computer coupled with one or two dimensional detector, or combinations thereof. In some embodiments, the data processing unit comprises a two dimensional detector. The two dimensional detector may be for example a charge-coupled device (CCD) or complementary metal oxide semiconductor (CMOS) camera, or the like. In certain embodiments, the data processing unit 150 is a multiple element (i.e., multi-pixel) camera.

Figure 2:
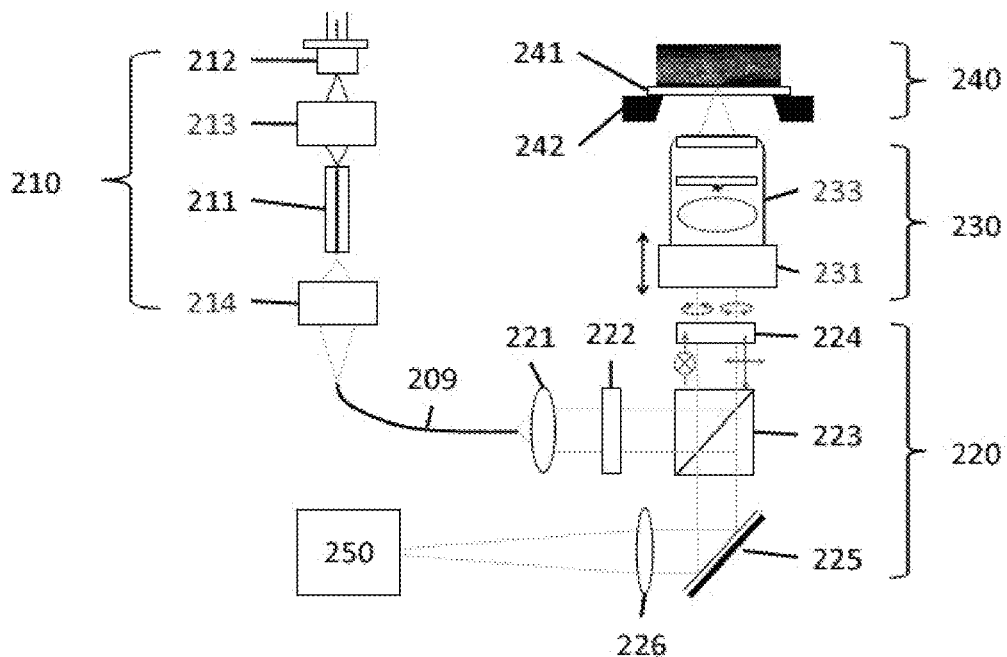
FIG. 2 illustrates a schematic drawing of an exemplary invention device/system.

FIG. 2 shows an exemplary invention system/device 200 comprising a crystal fiber/LED broadband light source 210 providing illumination light to an optical microscope module 220 via a multimode fiber 209, the optical microscope module 220, a Mirau type objective module 230, a tissue translation module 240 and a data processing unit 250. The exemplary light source module 210 comprises a $Ce^{3+}$:YAG single-clad crystal fiber 211 was pumped by a 1-W, 445-nm laser diode 212 (Nichia, #NDB7875, Japan) through a first collimating and focusing module 213, (e.g., including a 60× aspheric lens, a band-pass filter (Semrock, #FF01-445/45, America), and a 40× achromatic lens), and a second collimating and focusing module 214 (e.g., including 40× achromatic objective lens and 20× achromatic objective lens), where the function of band-wave-pass filter is to reflect the backward broadband light back to the single-clad crystal fiber 211, to collimate the fluorescence light output from the single-clad crystal fiber 211, and focus it in to the multimode fiber 209. The broadband light emerging from the output terminal of the single-clad crystal fiber was coupling into multi-mode fiber 209 and was then collimated by an objective lens 221 in an optical microscope module 220, where the center wavelength and bandwidth of light after single-clad crystal fiber are respectively 560 and 95 nm.

The exemplary optical microscope module 220 comprises an objective lens 221, an optical long-wave-pass filter 222, a polarization beam splitter 223, an optical switch 224 (e.g., TN-LC, PA-LC, VA-LC, IPS or an achromatic quarter wave plate, or other suitable device), which is set between the polarization beam splitter 223 and the Mirau type objective module 230 and directs light to a Mirau type objective module 230, a mirror 225, and a projection lens 226. The light output from multimode fiber 209 and reflected by the polarization beam splitter 223 became linearly polarized. The design of the optical switch 224 allows the invention device/system to toggle between OCT mode and orthogonal polarization spectral imaging (OPSI) mode. In some embodiments, the optical switch is a quarter-wave plate, or the like. For example, in the OCT mode, the fast axis of the quarter-wave plate (i.e., an example of the optical switch) is set to an angle of 45° with respect to the horizontal axis. In this mode, only the portion of the signal light with its polarization state unchanged after the reflection (or scattering) from the sample may pass through the polarization beam splitter 223, and be detected by the data processing unit 250. In the OPSI mode, the fast axis of the quarter-wave plate was set to be parallel (0°) or orthogonal (90°) to the horizontal axis. In this mode, only the portion of the signal light with its polarization state rotated by 90° after the reflection (or scattering) from the sample may pass through the polarization beam splitter 223, and be detected by the data processing unit 250. Therefore, the system in the OPSI mode is able to detect the depolarized light scattering in the sample. It is particular useful to imaging sample in depth structure (e.g., skin tissue structure) under OCT mode. However the toggle switch design with an optical switch allows the invention system to detect any substructures or micro-environments of the sample (e.g., red blood cells and microvascular) in its dynamite state thereof (e.g., red blood cells moving in the blood vessels) via obtaining contrast images of absorption, dispersion, and/or scattering therefrom.

After passing through the optical switch 224 (e.g., an achromatic quarter wave plate described herein), the light changed to circular polarization. The circularly polarized light became counter circular polarization when reflected back from reference and sample arms through a Mirau type objective module 230. The light beams from reference and sample arms both became linearly polarized which is orthogonally correlated to the incident light after passing through achromatic quarter wave plate again (see the arrows in FIG. 2). As a result, the back-reflected light beams from sample in a tissue translation module 240 and reference arms were combined after going through polarization beam splitter 223, reflected by the mirror 225, and then projected onto a data processing unit 250 (i.e., a CCD (Imperx, #ICL-B0620, 640×480 pixels, America) via projection lens 226, to generate the interferometric signal with a frame rate of 260 frame/s. During one period of interferometric carrier signal, there are 60 sampling frames.

The tissue translation module 240 comprises a cover glass 241 covering a tissue sample (e.g., a skin tissue) and a transversely motorized linear stage 242 on a tissue holder means. The tissue holder means can be any holder suitable to hold a tissue. For example, the tissue holder means is a slide used to hold a biopsy. In some instances, the cover glass is function as a slide. In certain embodiments, the tissue holder means is the cover glass. The tissue holder means, in some embodiments, is a cassette for retaining a tissue sample such as a specimen of surgically exposed tissue from a patient.

Figure 3:
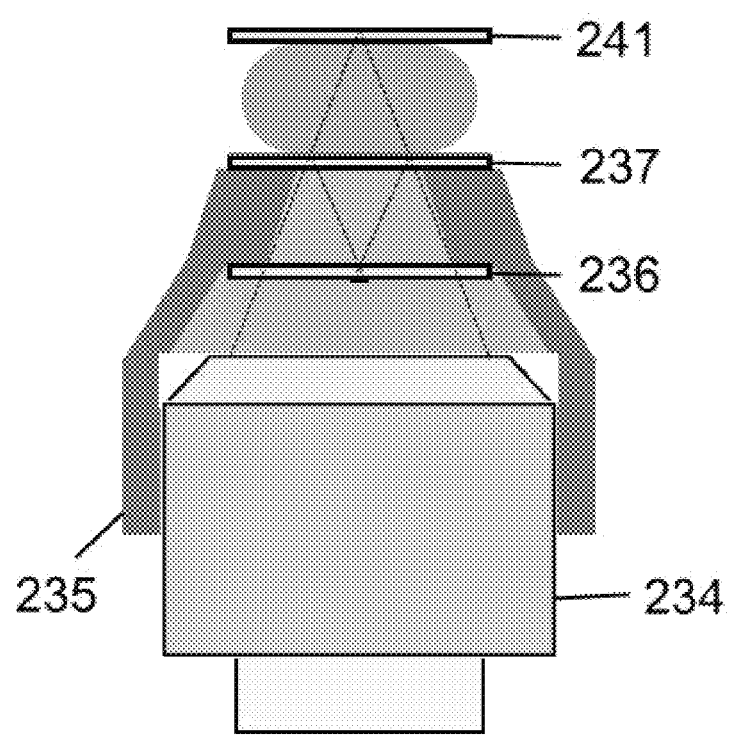
FIG. 3 shows a schematic drawing of an exemplary Mirau type objective module.

Referring to FIG. 3 which illustrates an exemplary Mirau type objective module of FIG. 2, the Mirau type objective module 230 comprises a z-axial piezoelectric transducer (PZT) 231, which is coupled with a 2D x-y linear platform 232, and an interference objective 233. For illustration purpose, the special designed Mirau type interference objective 233 comprises an objective lens 234 (e.g., Olympus, LUMPLFLN 20×W, NA: 0.5, field-of-view: 550 µm, Japan) immersed in a first media (e.g., water), a ring holder 235, two fused silica glass plates (thickness: 150 µm, $\lambda/10$ flatness, a first glass plate 236 and a second glass plate 237) to hold a second media (e.g., a silicone oil). The diameter of focal field in water is about 220 µm (⅓ field-of-view was used). The interference objective 233 was fixed on a z-axial piezoelectric transducer 231 (PI, #P-720, Germany). In some embodiments, the first media is the same as the second media. For example, both the first media and the second media may be silicone oil.

The cover glass 241 was laminated under the sample. In some embodiments, the cover glass has the same thickness as the glass plate. The total light travelling range of the PZT with open-loop control is 112 µm. A 500-µm-diameter black ink absorber (n=1.48) at the same planet of objective lens 234 is used to match the index of first glass plate 236 so as to absorb the stray light back to the data processing unit (i.e., a CCD), and for eliminating the DC term of intensity. After coating the interlaced layers by $TiO_2/SiO_2$, (T/R=60/40, T: transmittance; R: reflectance; $n_{silicone-oil}$=1.406), a broadband beamsplitter coating was coated on the top of second glass plate (227). The reflection coating of the first glass plate (226) contacting the second media (i.e., silicone oil) is about 4% as $n_{silicone-oil}$=1.406.

During operation, the objective lens 234 focuses the illumination light towards a test sample on the tissue translation module 240 through first glass plate 236. The second plate 237 reflects a first portion of the focusing light to the first glass plate reflection coating to define reference light and transmits a second portion of the focusing light to test sample to define measurement light. Then, the second plate 237 recombines the measurement light reflected (or scattered) from test sample with reference light reflected from the reflection coating on the first glass plate, and objective 234 and imaging lens image the combined light to interfere on a data processing unit 250 (e.g., a multi-pixel camera with or without a computer). The PZT 231 is coupled with a 2D x-y linear platform 232.

In some embodiments, the interference objective 233 comprises an objective lens 234 immersed in a media, a first glass plate 236, a second glass plate 237, in a sealed container filled with one or more media. The media described herein is defined as any media has characteristics to compensate for the dispersion in optical path introduced by the passage of the light beam through said media. The one or more media in the Mirau type objective module provides means for reducing the dispersion in the case of tomographic imaging in comparison with the traditional Mirau objective filled with air. In some embodiments, the invention Mirau type objective module comprises two or more media (e.g., the first media, the second media, and so on) where at least one media has optical characteristics similar to the sample to be analyzed, that is arranged to compensate for the dispersion in optical path introduced by the passage of the light beam through the Mirau type objective. Among various skin optical characteristics, refractive index is an important one. At the microscopic scales ranging from 1 to 10 µm, refractive index variation causes light scattering. Determination of the refractive indices of the human skin tissues is based on the known methods (e.g., Ding, et al., Physics in Medicine and Biology, 2006, 51 (6), 1479). It is about 1.38 to 1.44 in comparison with the refractive index of 1.00 of air at STP. Non exclusive examples of media with refraction indices between 1.3 to 1.5 include water (1.33), silicone oil (1.336-1.582, depending on compositions), 20% glucose solution in water (1.36), Ethanol (1.36), glycerol (1.47), Pyrex (1.47). In some embodiments, the refractive index of the media used in the Mirau type objective module in the range of about 1.0 to about 2.0, about 1.2 to about 1.8, about 1.3 to about 1.6, or about 1.3 to about 1.5. In certain embodiments, the refractive index of the media is in the range of about 1.3 to about 1.5.

For example, the objective lens 234 is immersed in water (i.e., a first media), or a liquid with optical characteristics close to those of water. This is because the sample to be imaged (e.g., living cells, skin tissues) contain mostly water. The imaging of the living cells can thereby be carried out in a satisfactory manner. In some embodiments, the one or more media is a liquid, a gel, a special glass, a special plastic, or any other suitable materials with optical characteristics close to those of testing sample. In certain embodiments, the media is a liquid. In some embodiments, the liquid media comprises water, glycerol, ethanol, silicone oil, or the like. In certain embodiments, the liquid media comprises water. In certain embodiments, the liquid media comprises silicone oil. In certain embodiments, the liquid media comprises glycerol. In some embodiments, the media is a transparent glass or plastics with a refraction index in the range of about 1.3 to about 1.5.

Figure 4:
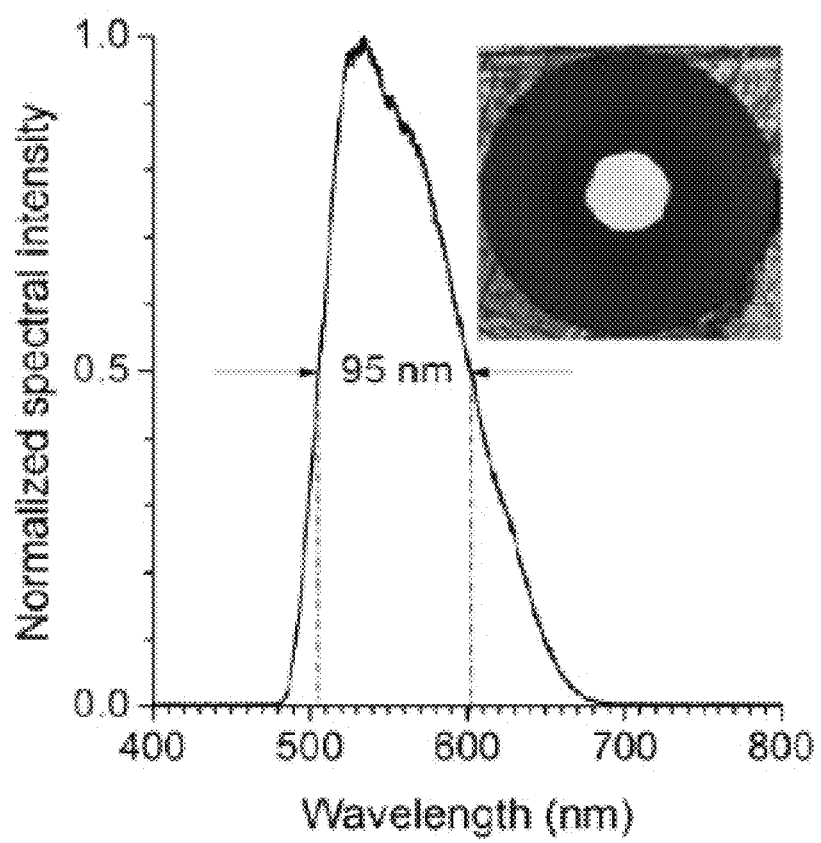
FIG. 4 shows the emission spectrum of an exemplary light source, a Ce3+:YAG single-clad crystal fiber where the inset shows the end view of the crystal fiber.
Figure 5:
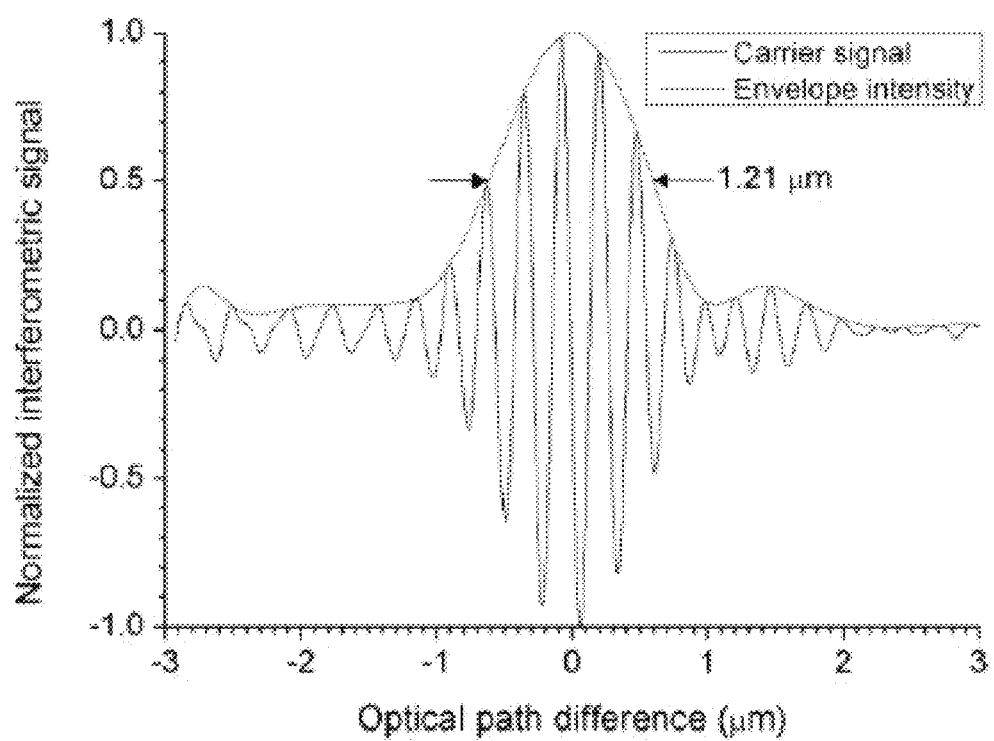
FIG. 5 shows the optical path difference between water and glass plate measured by one pixel of CCD.
Figure 6:
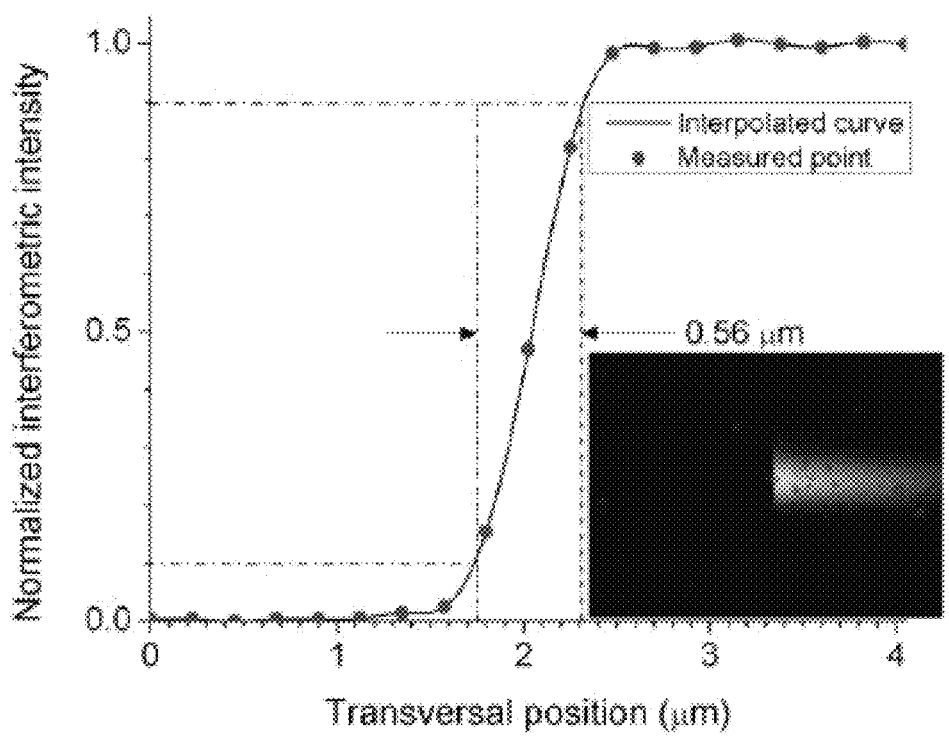
FIG. 6 shows the lateral scanning in water revealing the transversal resolution of 0.56 µm.

As illustrated in FIG. 2, the PZT 231 was biased by an amplified signal from a DAQ card (NI, #PCI-4461, America) with an open-loop mode. Z-axial position of the PZT versus input voltage was recorded by the counted wave numbers and phase difference of a He—Ne laser via Michelson interferometer. So, the hysteretic movement of the PZT was experimentally compensated via recorded position versus voltage curve. For example, FIG. 4 shows the emission spectrum of a Ce$^{3+}$:YAG SCF (an exemplary light source) where the insertion shows the end view of SCF. The interferometric signal intensity of A-scan reflected from the boundary between water and glass plate was measured by one pixel of CCD (see FIG. 5). The intensity of carrier envelope from carrier signal in FIG. 5 was calculated after band-pass filter and Hilbert transform or other phase demodulation algorithms. The detection sensitivity is about 81 dB calculated by the known methods. The noise floor of the invention system is substantially suppressed by stronger confocal gate (NA: 0.8 vs 0.5) effect, and then the effect of ghost image is further leveled down. The exemplary interference objective provides experimental resolutions of Ra=0.91 µm (see FIG. 5) and Rt=0.56 µm (see FIG. 6) along axial and transversal directions at the surface of water medium (or Ra=0.90 µm and Rt=0.51 µm at the surface of SC (n=1.47 after water hydration)), respectively; whereas, the theoretical spatial resolutions at the surface of water following diffraction limits are Ra=0.56 µm and Rt=0.43 µm (or Ra=0.55 µm and Rt=0.39 µm at the surface of SC) according to Equation 1.

$$\Delta z_{\mathit{eff}} = \left[ \frac{n_{water}}{n_{sample}\Delta z_{confocal}} + \frac{n_{sample}}{n_{water}\Delta z_{coherence}} \right]^{-1}, \quad (1)$$

where $\Delta z_{\mathit{eff}}$ means the effective axial resolution contributed by $\Delta z_{confocal}$ (confocal gate in water, equal to $\lambda_0 n_{water}/NA^2$, about 1.16 µm for 40× objective (NA: 0.8)) and $\Delta z_{coherent}$ (coherent gate in water, equal to $0.44\lambda_0^2/n_{water}\Delta\lambda$, about 1.09 µm for Ce$^{3+}$:YAG light source with the same objective). $n_{sample}$ and $n_{water}$ are the refractive indices of the sample and the water, respectively. $\lambda_0$ and $\Delta\lambda$ are the central wavelength and the bandwidth, of the light source. In FIG. 3, 40× interference objective lens 234 is used for water-immersion. It was surprisingly found that when 20× interference objective lens was used (where NA is 0.5) the sample scanning becomes more efficient but still achieves the similar 3-D imaging results (e.g., resolution). Thus, in some embodiments, the objective lens used for the invention device/system has NA of 0.5 or less. Because both water and silicone oil have similar refractive index similar to one of the sample tissue, a skilled person in the art would readily recognize to substitute one with the other, or use water only, or use silicone only, or use any other suitable media in accordance with the practice of the present invention. For example, an interference objective immersed in silicone oil (first media) with the second media of silicone oil was produced to overcome the easy evaporation of water based Mirau type objective module.

Typically, FF-OCT takes the en face image from calculating the stack information via phase-stepped technique with single-shot CCD at 0°, 90°, 180°, and 270, of which the phase was shifted by triangularly oscillated motion of PZT. As the exposed time of one en face image increases, the detection sensitivity becomes better. Then, 3-D image is reconstructed by piling up the en face images along z-axis. Different from classical FF-OCT, the invention device/system comprising a Mirau type objective reconstructs the 3-D image stack via sequential interferometric signals. This secondary consideration results a better in depth imaging invention device/system.

Figure 7:
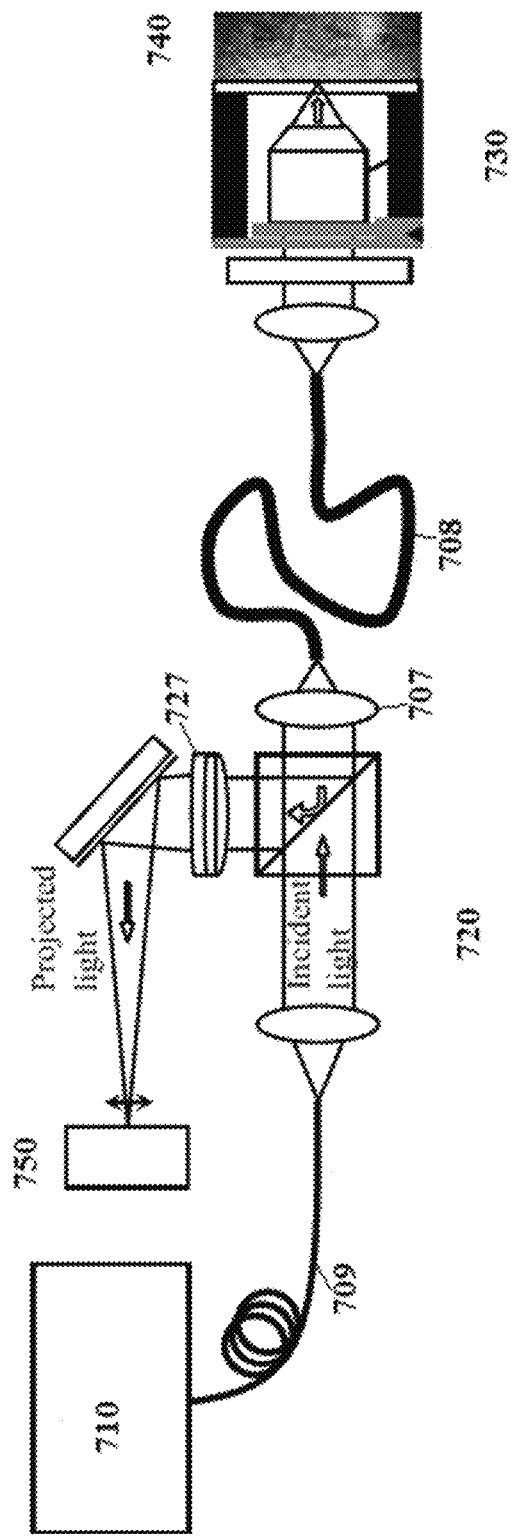
FIG. 7 illustrates a schematic drawing of a variation of the exemplary invention device/system shown in FIG. 2.

Referring to FIG. 7, which provide a variation of the embodiment shown in FIG. 2, an exemplary device/system comprises a crystal fiber/LED broadband light source module 710 providing illumination light to an optical microscope module 720 via a multimode fiber 709, a Mirau type objective module 730, and an imaging fiber bundle 708 transporting light between the Mirau type objective model, the optical microscope module, a tissue translation module 740 and a data processing unit 750. This variation embodiment provides a mobile/flexible Mirau type objective module to detect sample in vivo. To accommodate this design, a collimation lens 707 is used to further collimate light between the imaging fiber bundle 708 and the Mirau type objective module 730. As shown in FIG. 7 an optional focal lens 727 is used to further enhance the quality of the images.

The invention device or system is useful to imaging a tissue sample with ease. It is particular useful in aiding skin treatment. For example the invention device or system is useful as an aid for Mohs surgery. During the surgery, after each removal of tissue, while the patient waits, the tissue is examined for cancer cells, and that examination informs the decision for additional tissue removal. Mohs surgery is one of the many methods of obtaining complete margin control during removal of a skin cancer; it hinges on complete circumferential peripheral and deep margin assessment. The invention devices or systems can image the sample tissue either in situ or after removal from the patient thus provide an efficient way to aid Mohs surgery. In some embodiments provide a method for imaging a tissue sample comprising imaging test light in depth emerging from a sample, and imaging a contrast image of absorption, dispersion, and/or scattering from a substructure of the sample to provide a dynamic state of the sample, by a device or a system described herein. In some embodiments, the tissue sample is a skin tissue. In certain embodiments, the method is for imaging a skin tissue condition. In certain embodiments, the skin condition is determined by complete circumferential peripheral and deep margin assessment.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A device comprising a light source module configured to provide a source light to an optical microscope module, which handles the source light and processes light signals; a Mirau type objective module, which handles light from the optical microscope module and process light signals generated from a sample; and a data processing unit for analyzing light signals from the sample, wherein said Mirau type objective module comprises an interference objective immersed in a media.

2. The device of claim 1, wherein the light source module comprises an amplified spontaneous emission light source, a superluminescent diode, a light emitting diode (LED), a broadband supercontinuum light source, a mode-locked laser, a tunable laser, a Fourier-domain Mode-locking light source, an optical parametric oscillator (OPO), a halogen lamp, a $Ce^{3+}$:YAG crystal fiber, a $Ti^{3+}$:$Al_2O_3$ crystal fiber, or a $Cr^{4+}$:YAG crystal fiber.

3. The device of claim 2, wherein the light source module comprises a $Ce^{3+}$:YAG crystal fiber, $Ti^{3+}$:$Al_2O_3$ crystal fiber, or a $Cr^{4+}$:YAG crystal fiber.

4. The device of claim 3, wherein the light source module comprises a $Ce^{3+}$:YAG crystal fiber.

5. The device of claim 1, wherein said Mirau type objective module comprises an interference objective lens immersed in a media, a first glass plate, a second glass plate in a sealed container filled with one or more media.

6. The device of claim 1, wherein the interference objective lens immersed in a media has optical characteristics similar to the tissue sample to be analyzed.

7. The device of claim 6, wherein the optical characteristics comprise refractive index.

8. The device of claim 7, wherein the media has a refractive index in a range of about 1.2 to about 1.8.

9. The device of claim 8, wherein the media has a refractive index in a range of about 1.3 to about 1.5.

10. The device of claim 9, wherein the media comprises water, silicone oil, ethanol, glycerol, pyrex, a transparent glass or plastic with a refractive index in a range of about 1.3 to about 1.5, or combinations thereof.

11. The device of claim 10, wherein said media comprises water, silicone oil, glycerol, or combinations thereof.

12. The device of claim 11, wherein said media comprises silicone oil.

13. The device of claim 5, wherein the one or more media comprises a first media and a second media.

14. The device of claim 1, wherein said first media comprises water and the second media comprises silicone oil.

15. The device of claim 1, wherein the optical switch is a quarter-wave plate where the fast axis of the quarter-wave plate is set to an angle of 45° allowing a portion of a signal light reflected or scattered from the sample passing through with polarization state unchanged.

16. The device of claim 1, wherein the optical switch is a quarter-wave plate where the fast axis of the quarter-wave plate is set to an angle of 0° or 90° allowing a portion of a signal light reflected or scattered from the sample passing through with polarization state rotated by 90°.

17. The device of claim 1, wherein the optical microscope module further comprises an objective lens, an optical long-wave-pass filter, and a polarization beam splitter.

18. The device of claim 1, wherein the light source module comprises a $Ce^{3+}$:YAG crystal fiber, the optical switch is a quarter-wave plate, the Mirau type objective module comprises silicone oil as one or more media.

19. A system for imaging a sample comprising the device of claim 1.

* * * * *